United States Patent [19]
Allen

[11] 3,985,680
[45] Oct. 12, 1976

[54] OXIDATION CATALYST
[75] Inventor: George C. Allen, Corpus Christi, Tex.
[73] Assignee: Celanese Corporation, New York, N.Y.
[22] Filed: Oct. 16, 1975
[21] Appl. No.: 623,155

Related U.S. Application Data
[60] Continuation of Ser. No. 176,298, Aug. 30, 1971, abandoned, which is a division of Ser. No. 796,651, Feb. 3, 1969, Pat. No. 3,644,509.

[52] U.S. Cl. .............................. 252/456; 252/467; 252/471; 260/530 N
[51] Int. Cl.² .................... B01J 29/16; B01J 23/34; C07C 51/24
[58] Field of Search ................... 252/456, 467, 471; 260/530 N

[56] References Cited
UNITED STATES PATENTS

| | | | |
|---|---|---|---|
| 2,134,543 | 10/1938 | Andrews | 252/471 X |
| 3,271,446 | 9/1966 | Kerr | 252/471 X |
| 3,567,773 | 3/1971 | Yamaguchi et al. | 252/456 X |
| 3,579,574 | 5/1971 | Van der Meer | 252/471 X |
| 3,637,834 | 1/1972 | Pregaglia et al. | 260/530 N |

FOREIGN PATENTS OR APPLICATIONS

| | | | |
|---|---|---|---|
| 677,624 | 8/1962 | United Kingdom | 260/530 N |
| 1,107,478 | 3/1968 | United Kingdom | 260/530 N |

Primary Examiner—Carl F. Dees

[57] ABSTRACT

Disclosed is an oxidation catalyst which is particularly useful for the conversion of unsaturated aldehydes to the corresponding unsaturated carboxylic acid. The catalyst has the following empirical formula $Mo_a V_b W_c Mn_d O_e$.

6 Claims, No Drawings

OXIDATION CATALYST

This is a continuation of application Ser. No. 176,298, filed Aug. 30, 1971, now abandoned, which is a divisional application of application Ser. No. 796,651 filed Feb. 3, 1969, now U.S. Pat. No. 3,644,509.

The present invention relates to a process for the production of unsaturated carboxylic acids by the oxidation of unsaturated aldehydes and to a new and useful catalyst therefor.

Numerous processes and catalysts are known in the prior art for the production of unsaturated carboxylic acids from unsaturated aldehydes, e.g. the production of acrylic acid from acrolein. In these processes the aldehyde is oxidized to the acid in the presence of a catalyst such as that catalyst reported in Belgian Patent No. 698,273. The catalyst of the foregoing patent is one which has the empirical formula $Mo_nV_xW_yO_z$ wherein when $n$ is 12, $x$ is 0.5 to 12, $y$ is 0.1 to 6 and $z$ is 37 to 84. Although this catalyst is effective in the oxidation of unsaturated aldehydes to unsaturated acids, it suffers the disadvantage of a short active catalyst life.

It is thus an object of the present invention to provide a process for the production of unsaturated carboxylic acids from unsaturated aldehydes. It is a further object of the present invention to provide a novel catalyst for the oxidation of unsaturated aldehydes to unsaturated carboxylic acids which has an improved catalyst life.

SUMMARY

These and other objects are accomplished by the present invention which in one of its embodiments is a process for the conversion of a monoethylenically unsaturated acyclic aldehyde to the corresponding monoethylenically unsaturated acyclic carboxylic acid comprising reacting in the gas phase a monoethylenically unsaturated acyclic aldehyde with oxygen in the presence of a catalyst having the empirical formula $Mo_aV_bW_cMn_dO_e$, the atomic ratio of Mo:V:W:Mn:O being such that when $a$ is 12, $b$ is 0.5 to 12, $c$ is 0.1 to 6, $d$ is 0.5 to 20, and $e$ is 37 to 94. In another embodiment the present invention is said catalyst.

DESCRIPTION OF THE PREFERRED EMBODIMENT

As may be seen from the foregoing, the novelty of the present invention is mainly in the catalyst of the formula $Mo_aV_bW_cMn_dO_e$. This catalyst differs mainly from the prior art catalyst of Belgian Patent No. 698,273 by the inclusion of manganese as it has been discovered that the presence of manganese serves to greatly extend the active life of the catalyst. Although the general ranges for $a$, $b$, $c$, $d$, and $e$ have been given above it is preferred that the elements of the catalyst be present in atomic ratios such that when $a$ is 12, $b$ is a number from 1 to 6, $c$ is a number from 0.3 to 3.0, $d$ is a number from 1 to 12 and $e$ is a number from 40 to 84. The number of atoms of oxygen or the number assigned to $e$ is determined by the valence requirements of the molybdenum, vanadium, tungsten and manganese and is usually about equal to $3a$ plus $2.5b$ plus $3c$ plus $2d$.

The catalyst of the above empirical formula may be regarded as a mixture of oxides of the various metals and/or mixtures of heteropoly acid salts of the various metals. The catalyst may be prepared by any of the conventional methods such as by mixing aqueous solutions of the water soluble compounds of the metals followed by evaporation of the water so as to leave a dry cake which is calcined. Preferably the dry cake is granulated or pelleted before use and this may take place before or after calcining. As is well known calcining merely involves heating at high temperatures, e.g. 200° to 600° C in the presence of air or other gases containing molecular oxygen. Suitable water soluble compounds useful in the preparation of a catalyst in accordance with the foregoing method include ammonium paramolybdate, ammonium metavanadate, ammonium paratungstate, manganous acetate, ammonium metatungstate, orthotungstic acid, metatungstic acid, molybdic acid, molybdenum pentoxide, molybdenum trioxide, manganous benzoate, and manganese nitrate. When the catalyst is to be used for the oxidation of unsaturated aldehydes it is preferred that it be prepared by (1) forming an aqueous solution of an ammonium molybdate, an ammonium tungstate, an ammonium vandate and a water-soluble manganese salt of an inorganic or organic acid, (2) evaporating the liquid to obtain a solid which is (3) then calcined. Preferably manganese salts of $C_1$ to $C_8$ carboxylic acids or nitric acid are utilized as the source of manganese.

The catalysts of the present invention may be employed as such or may be used in connection with a suitable catalyst support although it is preferred that the catalyst be utilized without a support. Supported catalysts may be prepared by mixing a dry support or an aqueous slurry thereof with an aqueous solution of the desired metal salts followed by drying and calcining. Other methods for loading the catalyst on a support will also be obvious. Suitable supports include silica, alumina, silicon carbide, alumina-silica, titania, charcoal, clays, fire brick, bauxite, and the like. When a support is present as part of the catalyst composition, the support will usually comprise from about 25 to 99% by weight, preferably 50 to 95% by weight, of the catalyst composition. Of the various supports that may be utilized silica is preferred.

The process of the present invention may be carried out continuously or non-continuously and the catalyst may be present in various forms such as in one or more fixed beds or as fluidized system. Portions of the reactants which do not undergo reaction may be recycled if desired. The temperatures employed are preferably between 215° and 270° C although higher or lower temperatures generally between 200° and 350° C may be employed.

The pressure utilized in the process of the present invention may be subatmospheric, atmospheric or superatmospheric. Usually pressures ranging from 0.5 to 3.0 atmospheres will be utilized although pressures up to 10 atmospheres and higher may be suitably employed. The contact time of the reactions with the catalyst at the reaction conditions is generally between 0.3 and 15 seconds but is preferably a relatively short time of from 0.5 to 10 seconds. By contact time as used herein is meant the contact time adjusted to 25° C and atmospheric pressure (conditions denoted by NTP). Thus the contact time is calculated by dividing the volume of the catalyst bed (including voids) by the volume per unit time flow rate of the reactants at NTP.

The oxygen necessary as a reactant in the present process may be from practically any molecular oxygen-containing gas such as concentrated molecular oxygen or air. Also the molecular oxygen-containing gas may be one wherein molecular oxygen is mixed in varying amounts with an inert diluent gas such as nitrogen, argon, or a carbon oxide. The unsaturated aldehyde reactant may be premixed with the oxygen-containing gas before introduction to the reaction zone or the reactants may be introduced separately into the reaction zone. Also the unsaturated aldehyde and/or molecular oxygen may be introduced into the reaction zone at one or a plurality of points along the length of the reaction zone. The reactants may be pretreated before entering the reaction zone such as for the removal of undesirable components therefrom.

Although other unsaturated acyclic aldehydes may be oxidized to the corresponding carboxylic acids by the present process, the aldehydes preferably have $\alpha$-$\beta$-unsaturation with the most suitable aldehydes being of the formula:

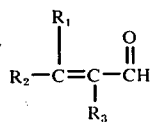

wherein $R_1$ is hydrogen or an alkyl radical of 1 to 6 carbon atoms and wherein $R_2$ and $R_3$ are hydrogen or methyl radicals. Preferably the present process is utilized for the production of acrylic acid from acrolein. Other conversions that may be accomplished include methacrolein to methacrylic acid, and crotonaldehyde to crotonic acid.

In conducting the oxidation reaction, the gaseous feed mixture should generally contain from 0.5 to 6 moles of oxygen per mole of the unsaturated aldehyde although the preferable range is from 1.0 to 4.0 moles per mole. Water is also desirably present in the gaseous feed in amounts of from 1 to 25, preferably 2 to 20, moles per mole of unsaturated aldehyde. In addition to water, diluents which are gaseous under the reaction conditions and are relatively inert may be introduced into the system. Suitable diluents include nitrogen, flue gas, $CO_2$, and paraffinic hydrocarbons.

CATALYST A

In accordance with Example 6 of Belgian Patent No. 698,273, a catalyst was prepared by mixing solutions of ammonium paramolybdate (42.4 g in 100 ml of water), ammonium metavandate (7.0 g in 100 ml of water), and ammonium paratungstate (6.1 g in 100 ml of water). A colloidal suspension of 30 g of silica was then added and the resulting suspension evaporated to dryness at 120° C in a stream of air. The catalyst was calcined at 400° C for 5 hours and screened to −20 to +30 mesh. The specific surface area of the catalyst was 50 m² per g. The catalyst may be represented by the empirical formula $Mo_{12}V_3W_{1.2}O_{47}/SiO_2$.

CATALYST B

A catalyst identical to that of Catalyst A was prepared except that the silica support was omitted.

CATALYST C

A catalyst was prepared as in Catalyst A except that in accordance with the present invention an aqueous solution of 15 g of manganese acetate tetrahydrate was mixed with the other aqueous salt solutions before evaporating to dryness. The catalyst obtained may be represented by the formula $Mo_{12}V_3W_{1.2}Mn_3O_{53}/SiO_2$.

CATALYST D

A catalyst of the present invention was prepared according to the procedure used for Catalyst C except that the silica support was omitted. The catalyst may be represented by the formula $Mo_{12}V_3W_{1.2}Mn_3O_{53}$.

CATALYST E

An unsupported catalyst was prepared in the same manner as Catalyst D except that the amount of manganese was increased by utilizing an aqueous solution of 45 g of manganese acetate tetrahydrate. The catalyst may be represented by the formula $Mo_{12}V_3W_{1.2}Mn_9O_{65}$.

The following examples for the conversion of acrolein to acrylic acid are given in order to illustrate the oxidation of unsaturated aldehydes in accordance with the present invention. In all of these examples the catalyst was used in a U-tube fixed bed reactor, the U-tube having a total length of about 60 inches. The feed mixture consisting of acrolein, air and water was premixed and preheated to the reaction temperature prior to the introduction into the reactor. The effluent of the reactor was cooled to about 5° C and both the condensate and vent gases analyzed by gas chromatography. Atmospheric pressures were utilized. In the examples conversion, selectivity and yield are defined as follows:

$$\text{Conversion, \%} = \frac{\text{moles acrolein converted}}{\text{moles acrolein fed}} \times 100$$

$$\text{Selectivity, mole \%} = \frac{\text{moles acrylic acid produced}}{\text{moles acrolein converted}} \times 100$$

$$\text{Yield, mole \%} = \frac{\text{moles acrylic acid produced}}{\text{moles acrolein fed}} \times 100$$

EXAMPLE I

A series of runs were made utilizing Catalyst C in order to evaluate it under varying conditions of contact time and temperatures. The feed composition was held constant throughout the run, the molar ratio of water to acrolein in the feed being about 4:1 and the molar ratio of oxygen to acrolein about 1:1. The results of the runs are shown in Table I below.

TABLE I

| Run No. | Temp °C | Contact Time, sec. (NTP) | Conversion, % | Selectivity, mole % | Yield, mole % |
|---|---|---|---|---|---|
| 1 | 264 | 2.4 | 15 | 59 | 10 |
| 2 | 288 | 2.4 | 35 | 89 | 29 |
| 3 | 304 | 2.4 | 98 | 86 | 84 |
| 4 | 285 | 4.7 | 75 | 83 | 62 |
| 5 | 300 | 4.7 | 100 | 83 | 83 |
| 6 | 262 | 9.5 | 55 | 81 | 45 |
| 7 | 285 | 9.5 | 99 | 85 | 84 |

The above runs involved a total time of about 65 hours and the catalyst was still active at the end of this period. In contract to this, when a series of similar runs were made in order to evaluate Catalyst A — a prior art catalyst containing no manganese — the catalyst showed a great loss of activity after about 24 hours of use. Thus the presence of manganese in the catalyst appears to extend the catalyst life.

EXAMPLE II

Three runs were made under identical conditions except that Catalyst B was used in one run, Catalyst D in one run, and Catalyst E in the other run. The contact time was 0.8 seconds (NTP) in all the runs and the temperature was about 255° C in all the runs. In these runs the feed composition was such that the molar ratio of water to acrolein was about 17:1 and the molar ratio of oxygen to acrolein was about 3.8:1. The results of the three runs are shown in Table II below.

TABLE II

| Catalyst No. | Composition | Conversion, % | Selectivity, mole % | Yield, mole % |
|---|---|---|---|---|
| B | $Mo_{12}V_3W_{1.2}O_{47}$ | 97 | 86 | 83 |
| D | $Mo_{12}V_3W_{1.2}Mn_3O_{53}$ | 99 | 94 | 93 |
| E | $Mo_{12}V_3W_{1.2}Mn_9O_{65}$ | 98 | 94 | 92 |

As may be seen from Table II, under a given set of conditions, the manganese-containing catalysts of the present invention will give higher one-pass yields of acrylic acid than those of the prior art.

I claim:

1. A catalyst composition comprising the empirical formula $$Mo_aV_bW_cMn_dO_e$$

wherein the atomic ratio of Mo:V:W:Mn:O is such that when $a$ is 12, $b$ is from 0.5 to 12, $c$ is from 0.1 to 6.0, $d$ is from 0.5 to 20 and $e$ is from 37 to 94.

2. The catalyst composition of claim 1 which is unsupported.

3. The catalyst composition of claim 1 on a silica support.

4. A catalyst composition having the empirical formula $$Mo_aV_bW_cMn_dO_e$$

wherein the atomic ratio of Mo:V:W:Mn:O is such that when $a$ is 12, $b$ is from 0.5 to 12, $c$ is from 0.1 to 6.0, $d$ is from 0.5 to 20 and $e$ is from 37 to 94.

5. The catalyst composition of claim 4 which is unsupported.

6. The catalyst composition of claim 4 on a silica support.

* * * * *